United States Patent [19]

Michelson

[11] Patent Number: 5,052,373
[45] Date of Patent: Oct. 1, 1991

[54] SPINAL RETRACTOR

[76] Inventor: Gary K. Michelson, 438 Sherman Canal, Venice, Calif. 90291

[21] Appl. No.: 506,779

[22] Filed: Apr. 10, 1990

Related U.S. Application Data

[63] Continuation of Ser. No. 225,922, Jul. 29, 1988, abandoned.

[51] Int. Cl.⁵ .............................................. A01B 17/02
[52] U.S. Cl. ..................................................... 128/20
[58] Field of Search ..................................... 128/17, 20

[56] References Cited

U.S. PATENT DOCUMENTS

| | | | |
|---|---|---|---|
| 2,053,868 | 9/1936 | Grasso | 128/20 |
| 2,450,194 | 9/1948 | Glaser | 128/20 |
| 2,642,862 | 6/1953 | Jackson | 128/20 |
| 3,766,910 | 10/1973 | Lake | 128/20 |
| 4,627,421 | 12/1986 | Symbas | 128/20 |
| 4,702,230 | 10/1987 | Pelta | 128/20 |
| 4,747,394 | 5/1988 | Watanabe | 128/20 |
| 4,852,552 | 8/1989 | Chaux | 128/20 |

FOREIGN PATENT DOCUMENTS 2302078  9/1976  France ................................. 128/20

Primary Examiner—Edward M. Coven
Assistant Examiner—Mark S. Graham
Attorney, Agent, or Firm—Lewis Anten

[57] ABSTRACT

An improved spinal retractor frame having detachable pairs of blade sets is disclosed in which the blades are self-engaging, automatically aligning, and rapidly attaching. The spinal retractor has a pair of arms which engage blades along the sides of the arms. The blades have a U shaped opening at their upper portions for aligning and engaging with the arms of the retractor as the arms are separated by a ratcheting mechanism.

11 Claims, 8 Drawing Sheets

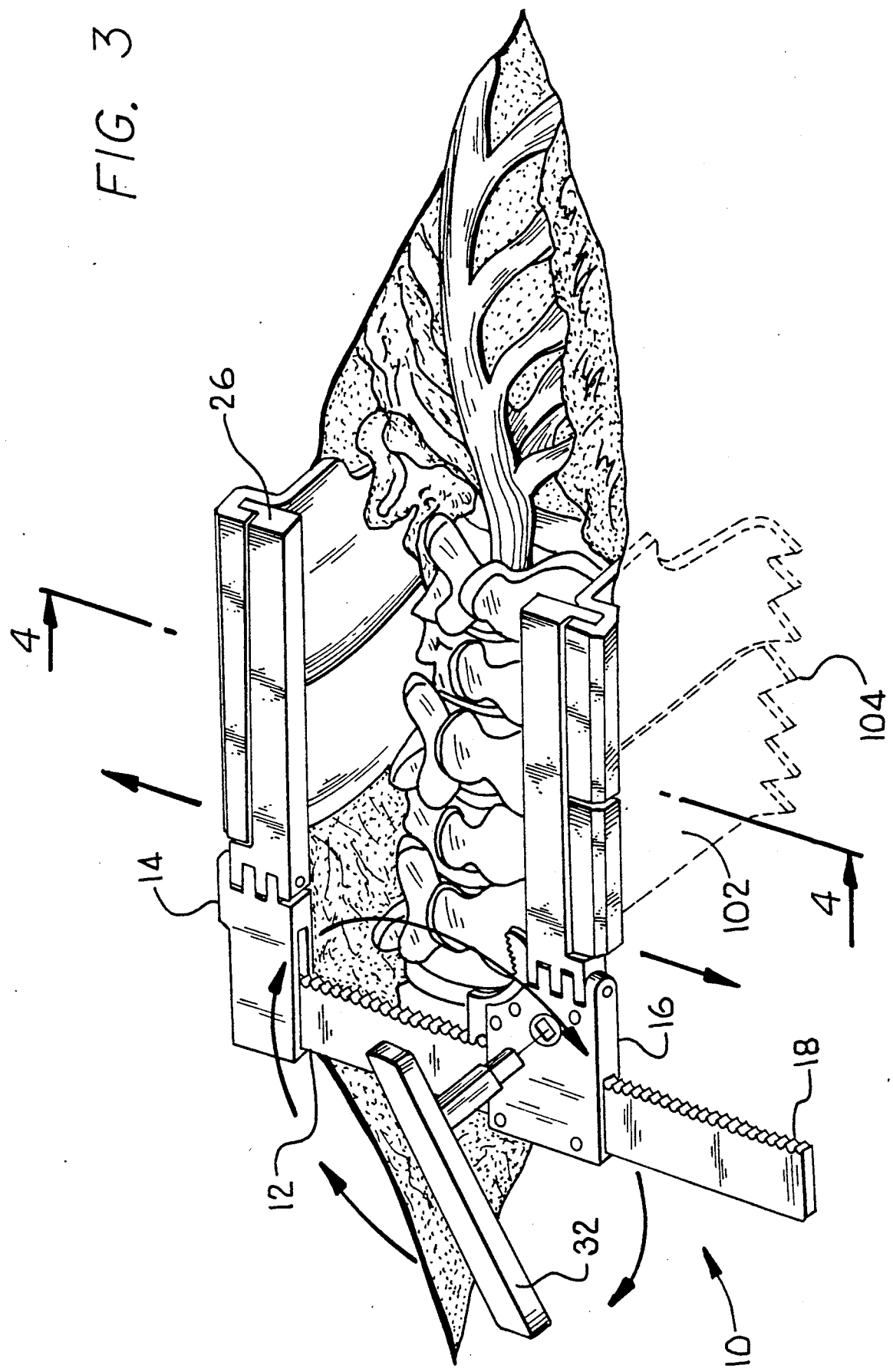

SPINAL RETRACTOR

This is a continuation of application Ser. No. 07/255,922, filed on July 29, 1988, now abandoned.

BACKGROUND

The performance of surgery requires that a retractor hold out of the way all tissues down to the actual surgical site. When performing a posterior approach to the thoracic or lumbar spine, it is necessary to retract very large and strong paraspinal musculature masses. Because of the differences in the size of patients and the relative mass of the muscles along various portions of the spine, it would be necessary to have a series of retractors with permanently attached blades or series of blades that could be attached or removed as needed from a basic blade-holding retractor frame. However, to keep the retractor blades from ejecting from the wound under the pressures generated by the muscle retraction, it is necessary to have the blades both diverge from the center line distally, and further to have large sharp teeth at a right angle to the longitudinal access of the blades so as to lock the blade tips beneath the muscle masses.

If the blades are divergent distally and in addition are splayed, then even with the retractor fully closed, the blades, if pre-attached to the retractor, would not be insertable into the wound as the outside of the tips of the blades would be further apart than the wound is wide. Therefore, retractors having pre-fixed blades must compromise the blade contour to fit in the wound by having less divergent and less angulated blades. Such a configuration significantly diminishing the ability to function as a deep wound retractor. Thus, spinal retractors with attachable blades have been devised.

At present, there are essentially two types of large spinal retractors with attachable and removable blades. Such retractors and blades are shown in FIGS. 10 and 11.

The first type (shown in FIG. 11) consists of a blade with a rectangular shaped opening at the top into which the retractor arms can be slid to hold the blade. While this does allow the blade to be inserted into the wound first and the retractor arms then attached, there can be great difficulty in attaching the blades to the retractor arms as both blades must be engaged simultaneously which requires that the blades and the arms of the retractor be opened to exactly the same width. Further, the blades must be parallel to each other and to the retractor and at the same time must protrude from the wound to exactly the same height. Further, the blades must be absolutely perpendicular to the spine, and not be rotated. Achieving all of these conditions at the same time can be quite difficult and time consuming.

There is also a retractor set which uses a rectangular open box-like attachment method, where the blades are strips of metal of similar widths and different lengths such that a series of strips are attached to each arm until a whole blade is essentially constructed, contoured to the particular patient. However, since the blades are attached to the retractor prior to insertion, the blades cannot be optimally divergent thereby defeating at least one of the two major advantages sought to be obtained from the use of the attachable blades.

The second type of large spinal retractor currently in use (FIG. 10) utilizes a set of attachment posts protruding from the retractor arms which then engage a series of corresponding holes on the top surface of the blades. However, when these blades are placed within the wound first and then an attempt is made to attach the retractor, there is considerable difficulty in aligning the blades and achieving the necessary three dimensional parallelism so as to attach the blades to the retractor. Furthermore, the exposed pegs and locking mechanism pose a threat to the surgeon as it is possible to rupture a glove on the exposed mechanism.

SUMMARY OF THE INVENTION

The present invention is a spinal retractor consisting of a large gear operated frame and a series of detachable, modular, and complimentary blades especially designed to facilitate attachment of the blades to the retractor without compromise to the angulation of the blades and consistent with optimal function. The retractor frame has a solid spine which is ratcheted, and one fixed arm and one movable arm attached perpendicularly to the spine. The movable arm is moved by a gear driven mechanism, and secured with a spring loaded lock which engages the ratchet of the spine. The retractor is opened and closed with a handle that is removable so that it will protrude during the surgery.

Both arms are hinged proximate the junction to the frame to allow the retractor frame and its arm to contour to the shape of the patient, assuring a low profile when in use.

The blades are widely divergent deeply and have teeth splaying outward beyond the divergence of the blades, substantially at right angle to the vertical plane of the blades themselves. The arms have a depression or cutout portion along one side of substantially their entire length. The blades have a substantially U-shaped configuration along their upper portion for engaging the corresponding depression or cutout on the arms. The separation of the arms results in the automatic, three dimensional alignment of the blades so as to firmly engage the blades on the arms.

OBJECTS OF THE INVENTION

It is a purpose of the present invention to provide for a spinal retractor and blade set that is easier and faster to use.

It is another purpose of the present invention to provide an improved spinal retractor and blade set that is more efficient, both in executing its purpose and in its method of attachment of the blades to the retractor.

It is another purpose of the present invention to provide for an improved spinal retractor and blade set that is modular in design so as to allow pairs of blades to be assembled in various combinations to enhance the overall variability.

It is still another purpose of the present invention to provide for an improved spinal retractor and blade set that is stronger than any presently existent spinal retractor.

It is yet another purpose of the present invention to provide for an improved spinal retractor and blade set that is of a low profile and without surface projections so as to minimize interference with, and risk to, the surgeon.

It is another purpose of the present invention to provide for an improved spinal retractor and blade set in which the blades divergence beyond previously existing retractors.

It is another purpose of the present invention to provide for an improve spinal retractor and blade set that is capable of opening a wound more widely than any previously existent spinal retractor.

These and other objects of the present invention will be apparent from a review of the following specification and the accompanying drawings.

BRIEF DESCRIPTION OF THE DRAWINGS

FIG. 3 is a perspective view of the retractor and blades in relation to the spine demonstrating the use of the hand crank to open the retractor.

DETAILED DESCRIPTION OF THE DRAWINGS

Figure 1:
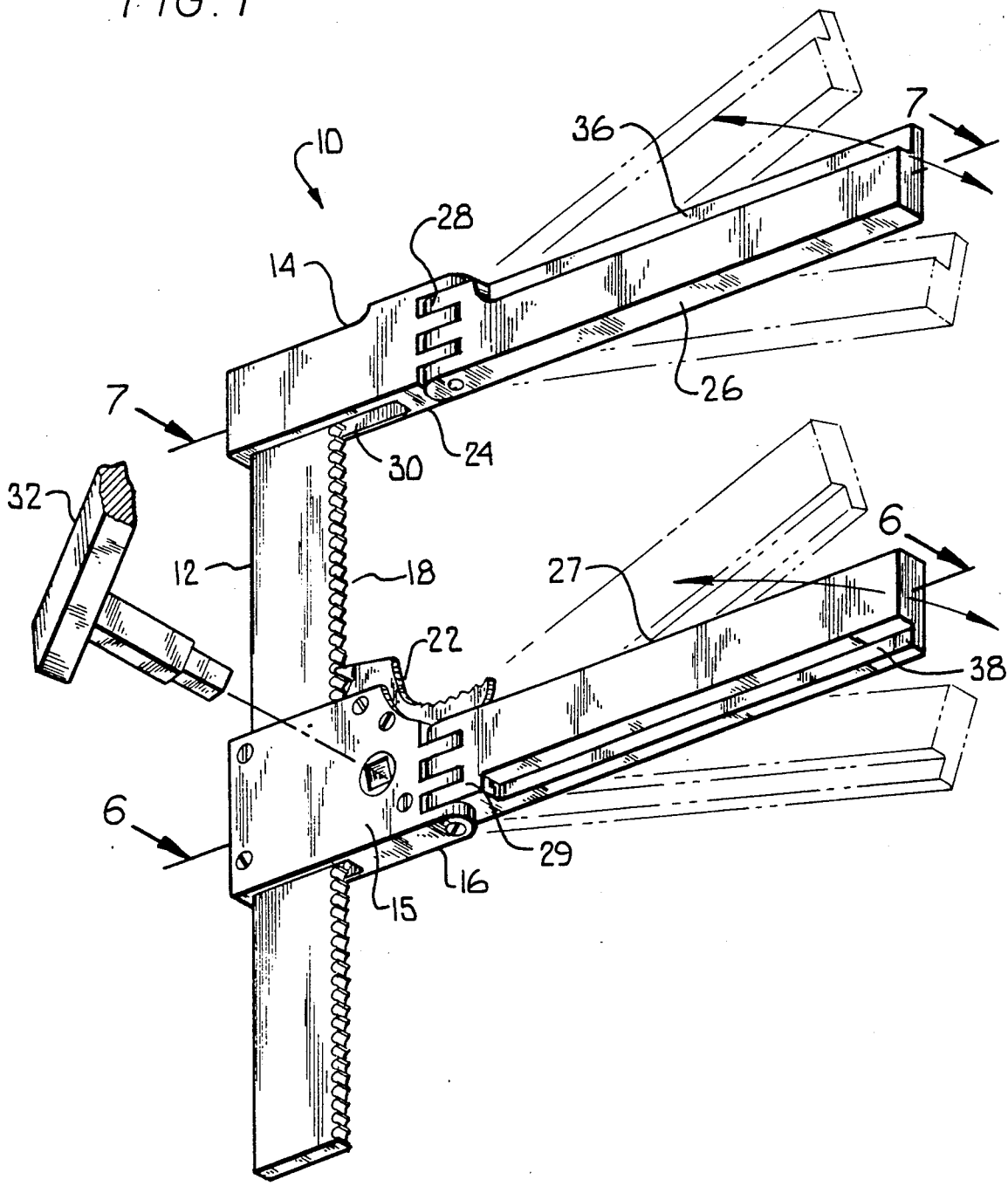
FIG. 1 is a perspective view of the retractor.

Referring to FIG. 1 the retractor frame 10 is shown in perspective view. The retractor frame 10 comprises a spine 12 having a rectangular cross section. A first fixed arm 14 is affixed to the upper portion of the spine 12 and a second movably arm 16 is movably attached to the spine 12. The two arms 14 and 16 have a substantially rectangular cross section and are parallel to one another and in the same plane.

The spine 12 has a ratchet 18 along its inside surface, which engages a complementary ratchet mechanism on the movable arm 16. The ratchet mechanism 20 (shown in FIGS. 6, 8 and 9) on the movable arm is lockable by lock 22 against movement.

The two arms 14 and 16 consists of a first rigid portion and a second hinged portion 26 and 27. The hinged portion 26 and 27 are connected to the first rigid portion 24 and 25 by hinges 28 and 29.

The hinged portions 26 and 27 have an elongated cutout or groove portion 36 and 38 along opposing sides of the hinged portions of the arms. The cutout or depressions extends substantially along the entire length of the edge of the hinged portion 26 and 27 of arms 14 and 16.

A hand crank 32 engages the drive gear opening 34 in the ratchet mechanism 20 for turning the gear mechanism to cause the movable arm 16 to move up and down the spine 12.

Figure 6:
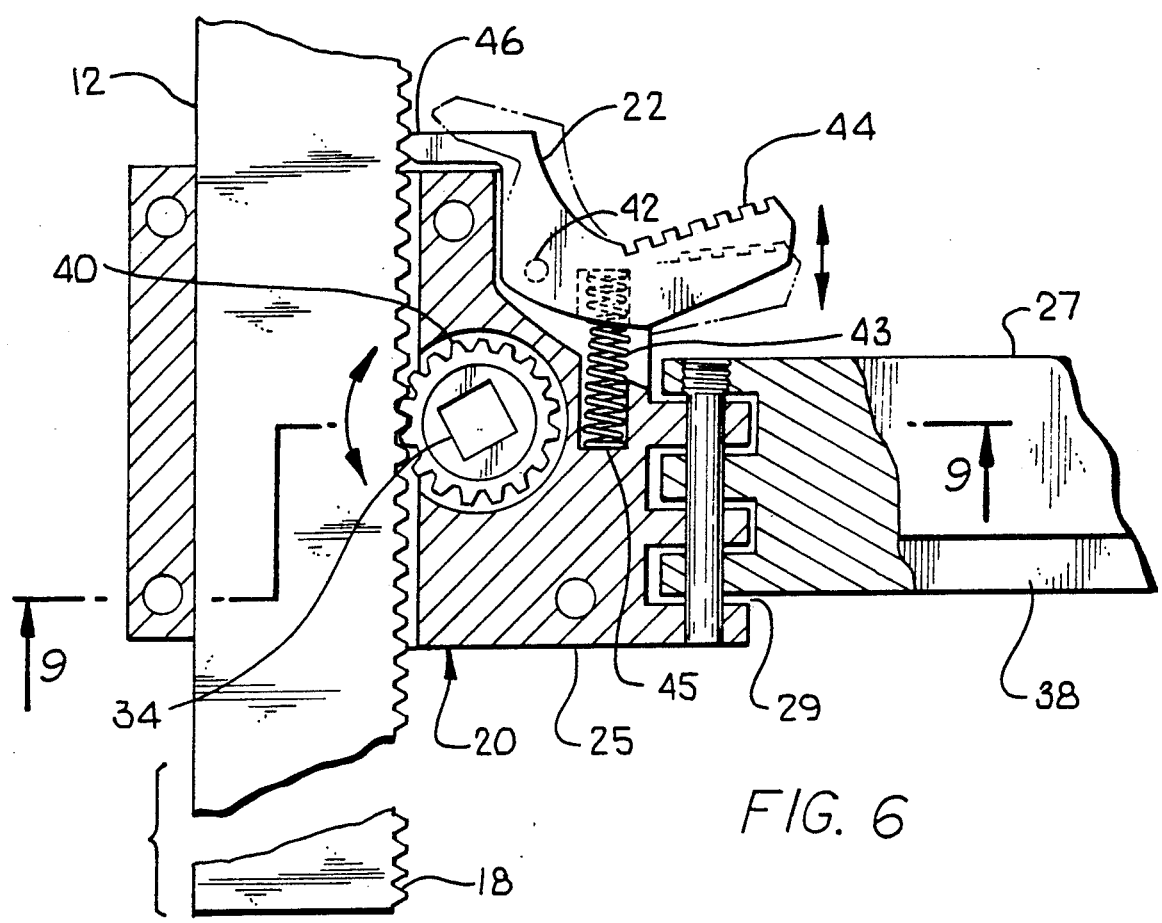
FIG. 6 is a partial sectional view of the retractor ratchet mechanism and lock mechanism.
Figure 8:
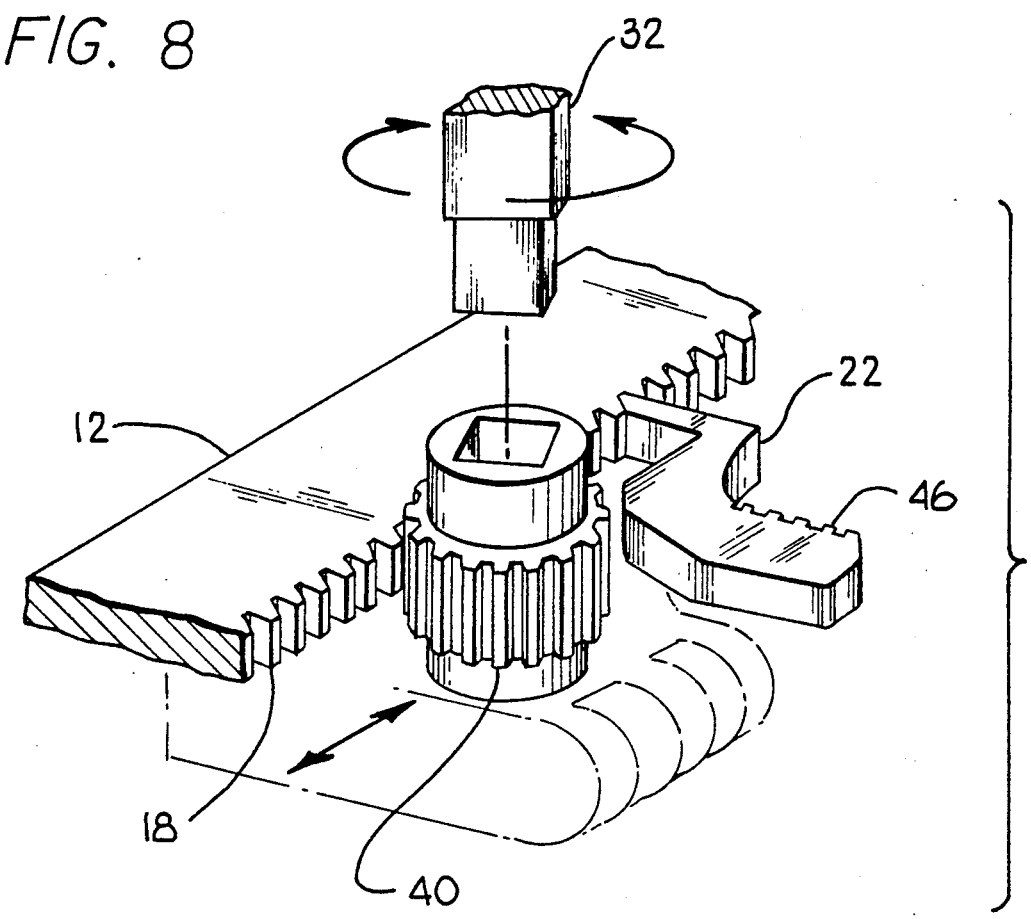
FIG. 8 is a partial sectional view of the ratchet and lock mechanism.
Figure 9:
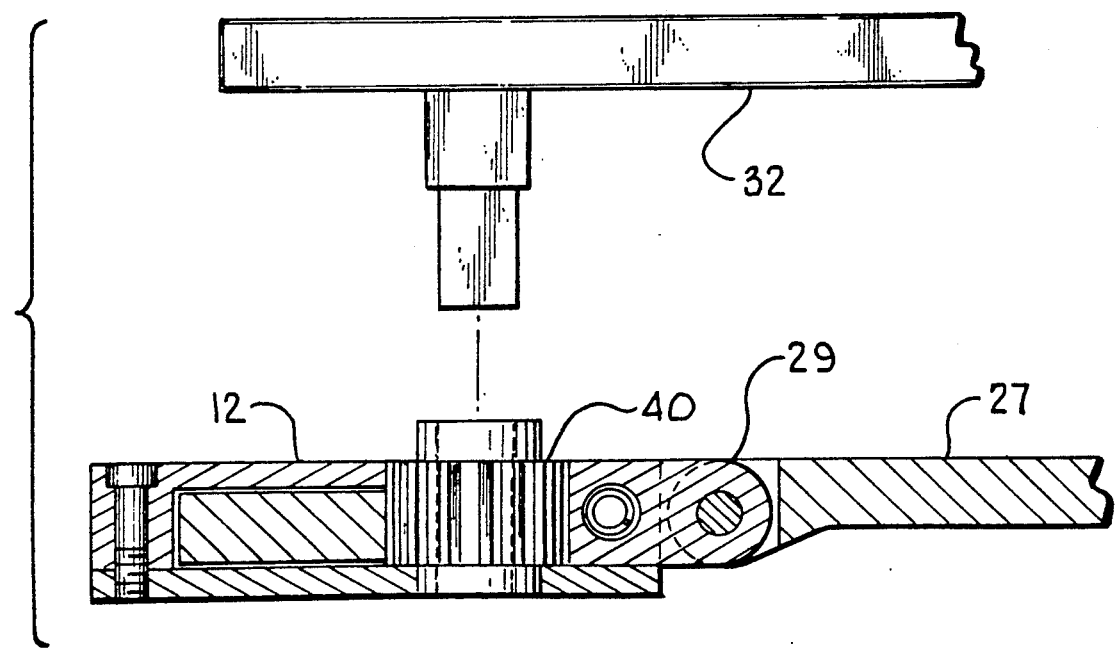
FIG. 9 is a side sectional view of the hand crank and its relationship to the gear.
Figure 10:
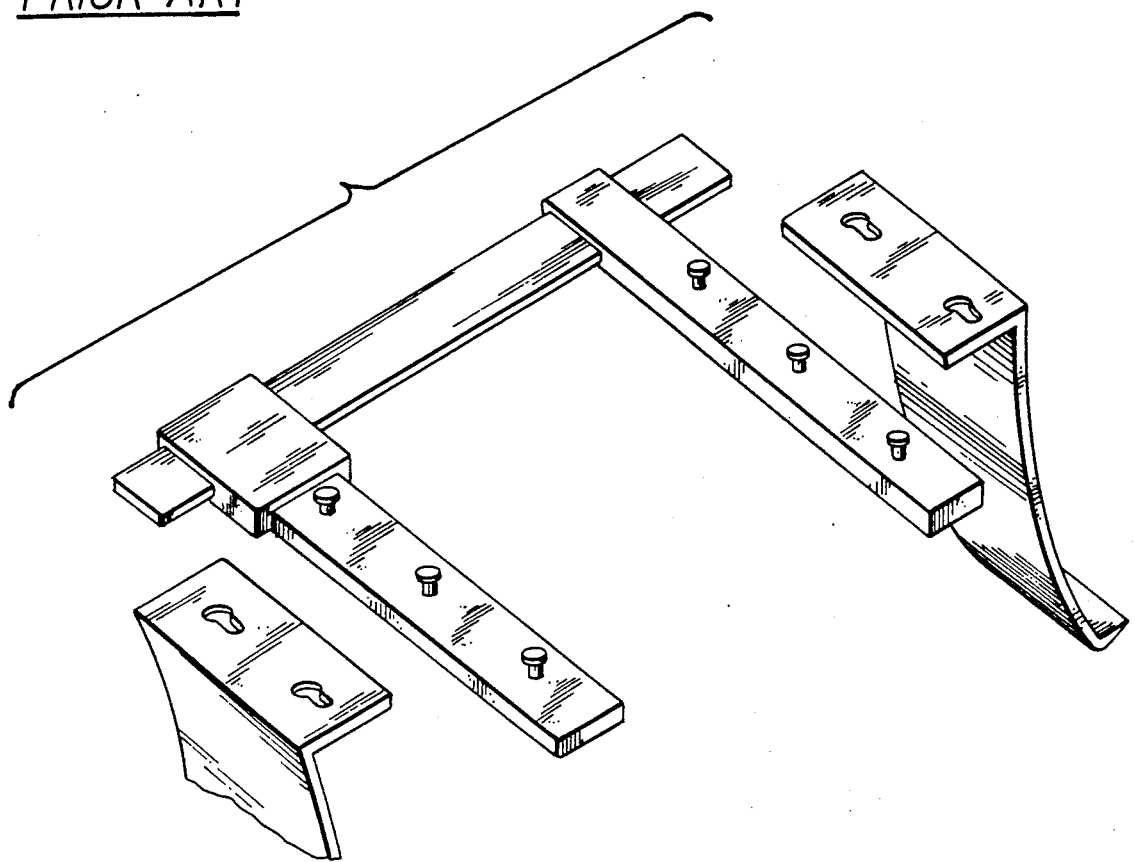
FIG. 10 is a perspective view of one version of the prior art.
Figure 11:
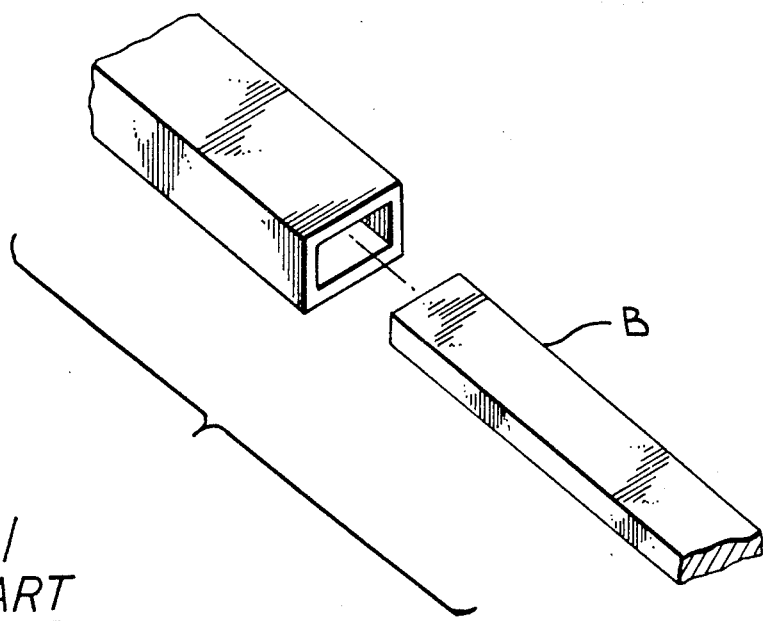
FIG. 11 is a perspective view of a second version of the prior art.

Referring to FIGS. 6, 8 and 9, the ratchet mechanism 20 is shown in detail. The ratchet mechanism 20 consists of drive gear 40 having a drive gear opening 34 for engagement with the crank 32. The drive gear 40 is complementary to the ratchet 18 along the spine 12.

The lock 22 is pivotable about pivot pin 42 and biased in a position wherein the lock engages the ratchet 18 by spring 43 enclosed within recess 45 in the rigid portion 25 of arm 16. A thumb depressing portion 44 is at one end of the lock and the other end of the lock 22 consists of a ratchet engaging tip 46 complementing the ratchet 18 of the spine 12, and biased at an angle so that the lock prevents closing of the arms when engaged, but not the opening of the arms.

Figure 7:
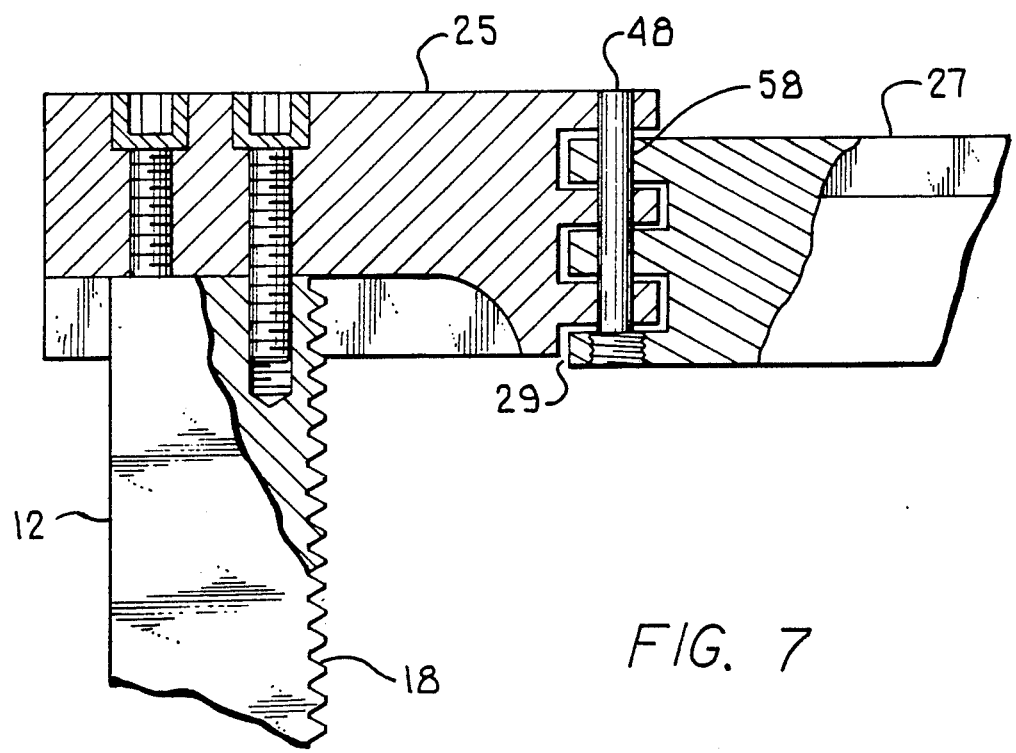
FIG. 7 is a partial sectional view of the "fixed" arm.

Referring to FIG. 7, the detail of the hinge 28 is shown. The hinge in both the fixed arm 14 and the movable arm 16 consists of a central pin 48 passing through larger aligned openings 58. The pin 48 may be held in place by screw threads or other conventional means.

Figure 2A:
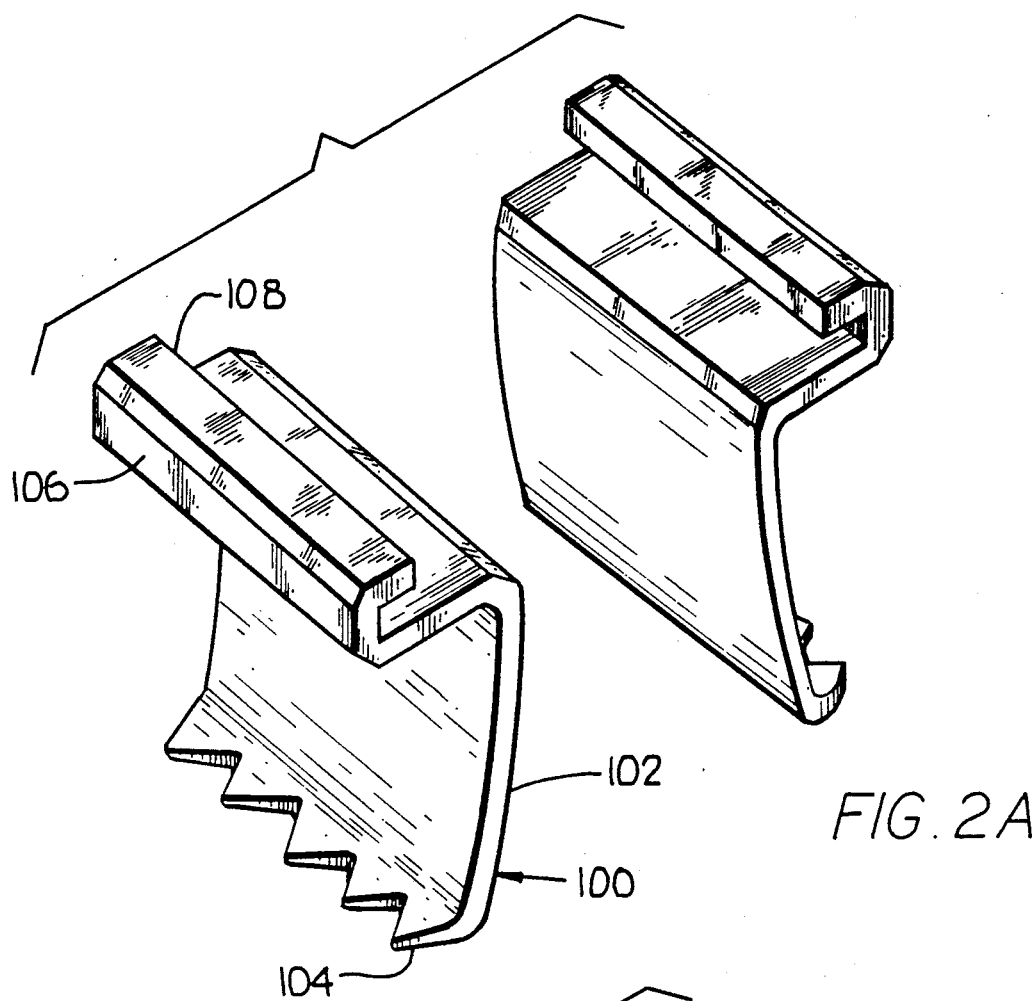
FIGS. 2a, 2b, and 2c are perspective views of various blade configurations used with the retractor of FIG. 1.
Figure 2B:
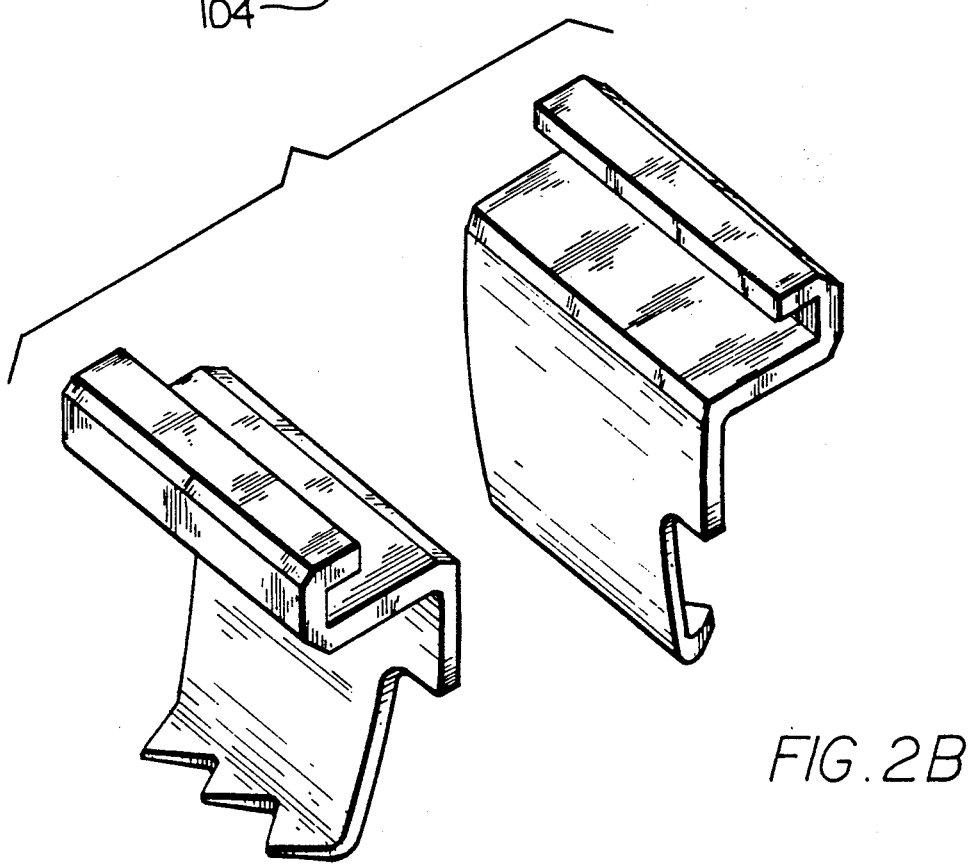
Figure 2C:
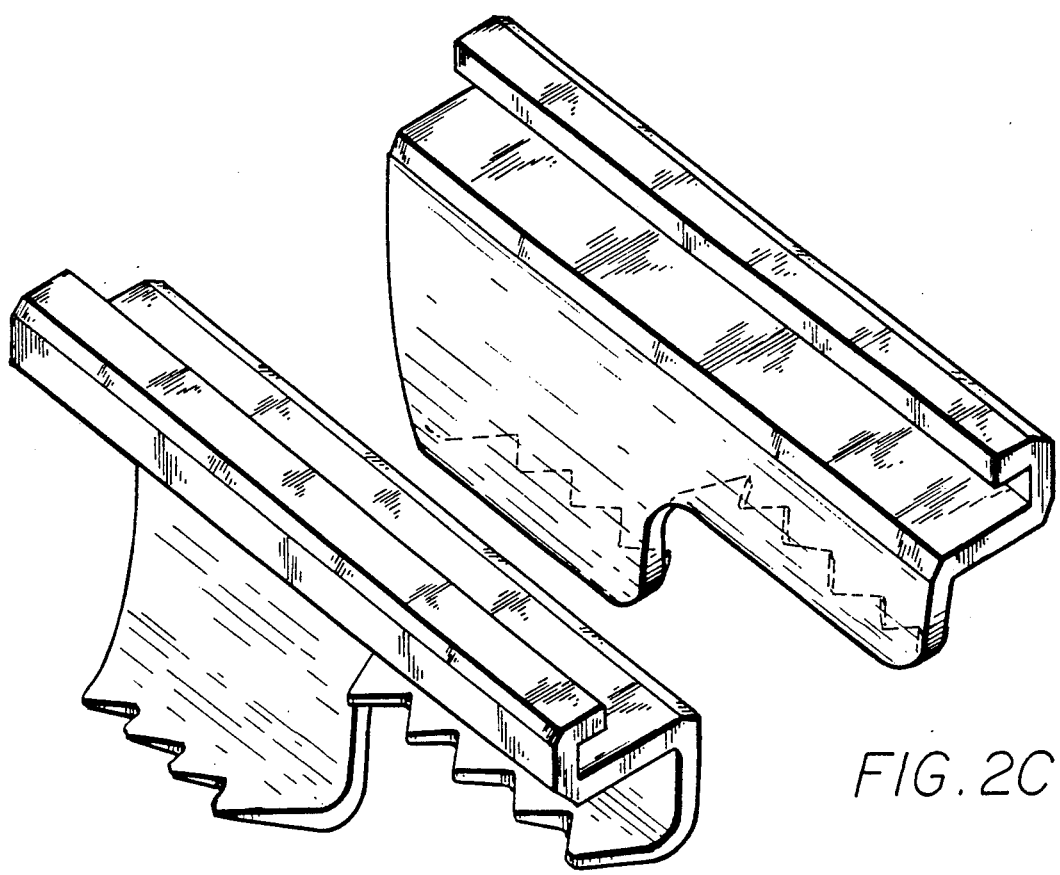

Referring to FIGS. 2(a)-2(c) alternative forms of blades are shown for use with the retractor. The blades 100 are used in pairs. One blade is used in association with the fixed arm 14 of the retractor frame 10 and the second blade is used in association with the movable arm 16 of the retractor 10.

The blade 100 has a substantially central planar portion 102, substantially perpendicular teeth 104 on the lower end and a U shaped engaging portion 106 at its upper end. The depth of the U shaped engaging portion 106 of the blade 100 is approximately ¾ inches, slightly smaller than the width of the cutout 36 and 38 of the retractor arms 14 and 16. In the preferred embodiment the cutout has a depth of approximately ½ inch. The teeth 104 are substantially perpendicular to the planar surface 102 and are approximately ½ inch long.

The blades are also made of heavy stainless steel, so as to resist bending by the muscles. The blades themselves are approximately ¼ inch thick and are approximately 4 inches wide.

The spine 12 is approximately one foot long and the maximum extension of the opening between the arms in use is approximately 6 inches. The length of the arms are approximately 6 inches long.

The recess or cutout portion 36 and 38 permits the arms 14 and 16 when the blades 100 are attached to the arms 36 and 38. Otherwise, the upper leg 108 of the blades 100 would extend beyond the top surface of the arms 36 and 38.

The width of the planar portion at the lower end may vary depending on the particular application for which the blades are being used, such as is shown in FIGS. 2b and 2c.

Figure 4:
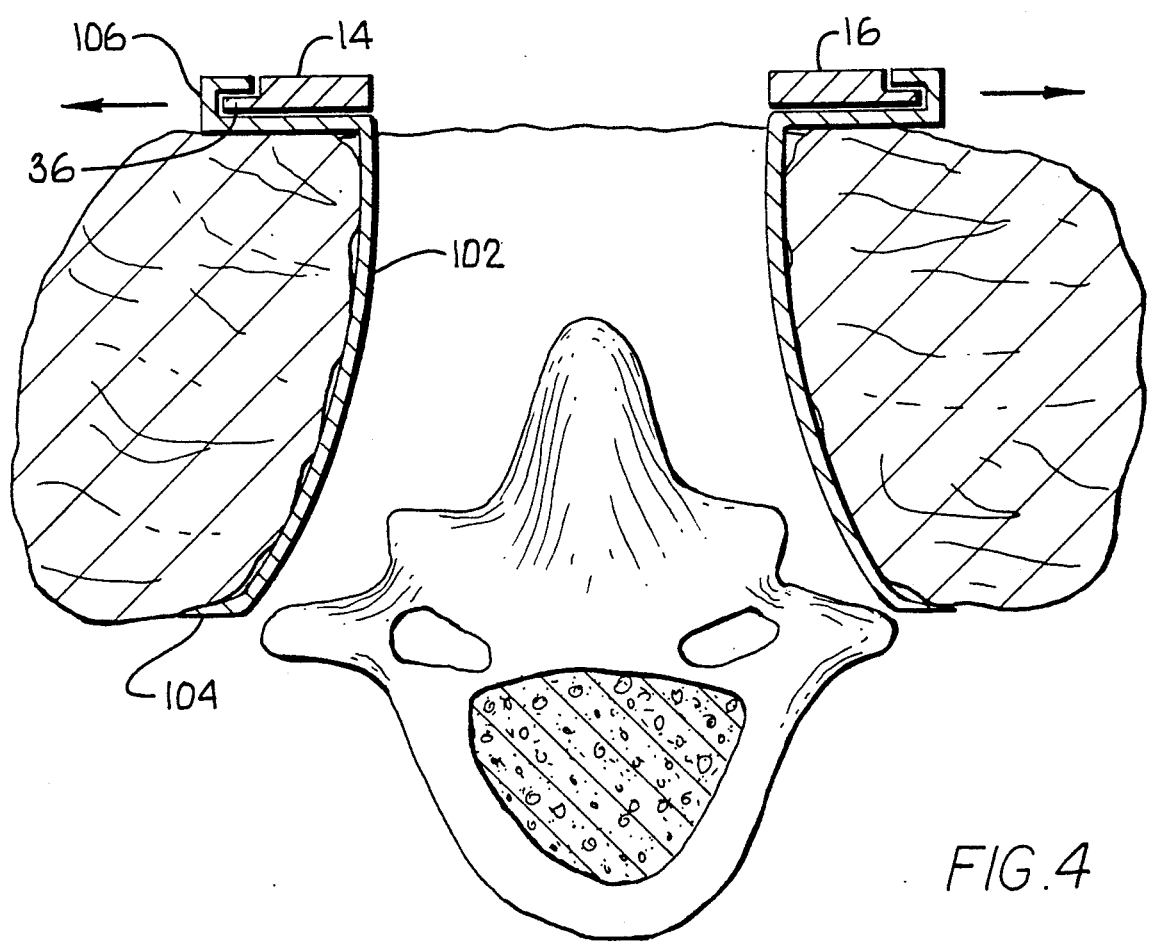
FIG. 4 is an cross sectional view of the lumbar spine demonstrating the cross sectional relationship between the retractor blades and the retractor arms.
Figure 5:
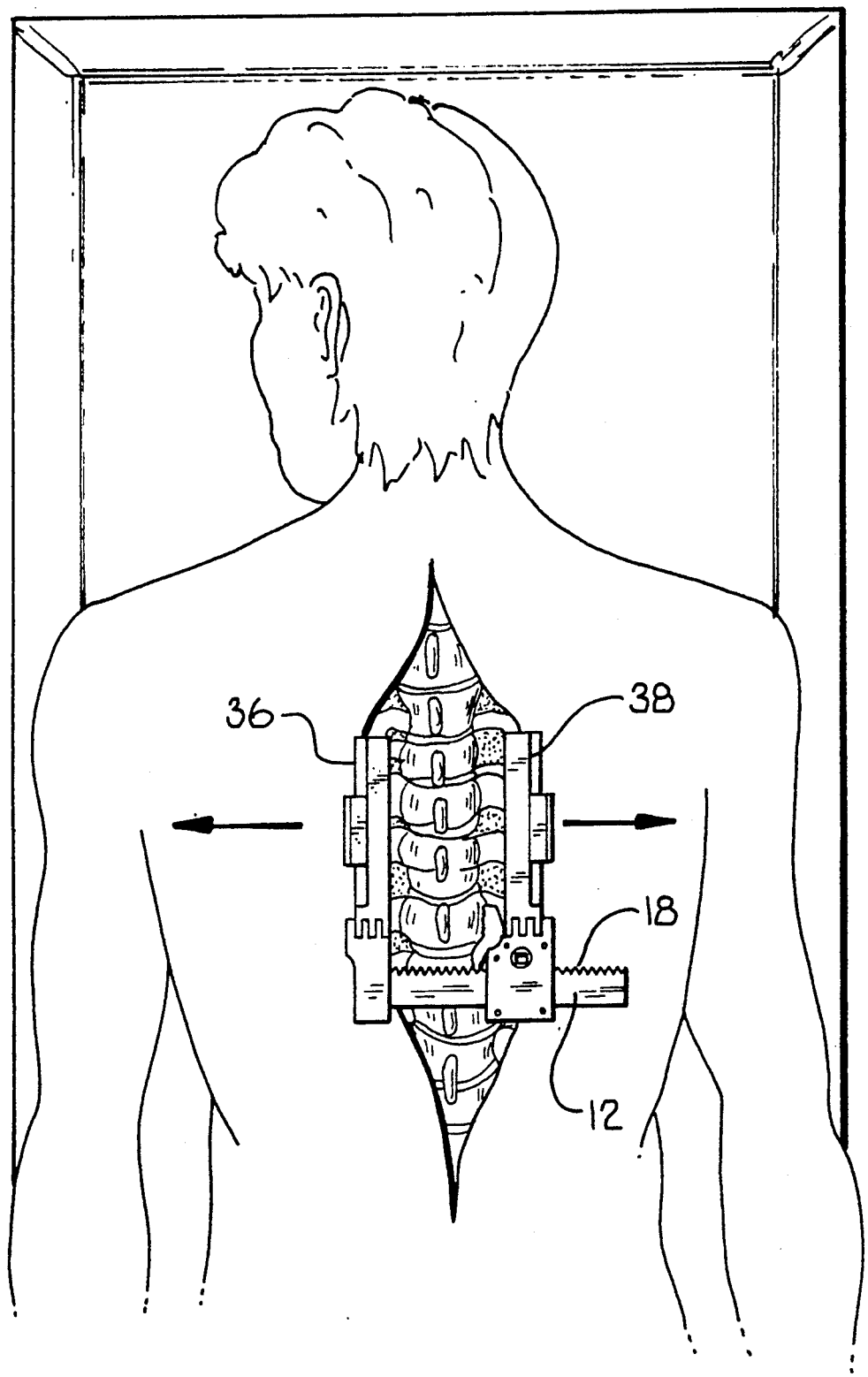
FIG. 5 is a top view of the retractor and blades situated in the thoracic spine.

Referring to FIGS. 3-5 the apparatus is shown in use on the patient. In FIG. 3 the retractor is shown in the spine, with the hand crank 32 about to be engaged. The teeth of the blades are illustrated as holding the muscles out of the way. In FIG. 4 the blades are shown inside sectional view, showing in detail the engagement of the arms with the blades. In FIG. 5, a top view of the retractor frame and blades during an operation.

METHOD OF USE

Blades of the appropriate depth as determined by the size of the patient are inserted on either side of the spine against and beneath the spinal musculature. The blades are inserted in pairs on opposite sides of the wound. The retractor frame is then placed between the blades in a closed position. The retractor is opened and when any part of the retractor arm rides over the inner portion of the U-shaped blade engagement area, the retractor arm will then de-rotate, align, and engage the blades as the retractor is opened. To remove the retractor, the crank is again inserted. The lock mechanism is released and the retractor allowed to close until the blades are disengaged. The retractor may then be removed, followed by the blades.

In the preferred embodiment, the retractor is made of heavy metal, such as stainless steel giving the retractor substantial weight to resist the torques that are applied by the muscle of the body.

While the present invention has been described in reference to the preferred embodiment of the invention, it is recognized that other embodiments of the present invention may be made without departing from the present inventive concept.

What is claimed is:

1. A surgical retractor comprising: a spine member, said spine member having a pair of arms movably attached substantially perpendicular to said spine member parallel to one another, both of said arms having a blade aligning means adapted for aligning separable blades, said separable blades having a top, slot-defining portion with a first thickness, said blade aligning means comprising a narrowed portion in the shape of a depressed cut out segment at least substantially the thickness of said first thickness of said top, slot-defining portion of said blades along substantially the length of said arms along the outer portion of said arms.

2. The apparatus of claim 1 in which one of said arms is fixed in relationship to said spine and the other of said arms is movable in relationship to said spine, and both of said arms have a hinged portion permitting movement of a portion of said arms of the plane of the arms and spine.

3. The apparatus of claim 2 in which said movable arm is movable by a gear mechanism.

4. The apparatus of claim 1 in which said arms have a substantially rectangular cross section and said narrowed portion is along the side of each arm away from the other arm.

5. The apparatus of claim 1 including at least one pair of blades, each of said blades having alignment means for engaging said aligning means on said arms, said blades engaging the narrowed of portion of said arms.

6. The apparatus of claim 5 in which at least one of said blades comprises a substantially planar member, said planar member having teeth at one end and said aligning means at the other end for engaging one of said arms, said aligning means being U shaped.

7. The apparatus of claim 6 in which said U shaped aligning means comprises an upper portion and a side portion and a bottom portion, defining an opening on one side of said U shaped aligning means, said opening of said U shaped aligning means faces one of said arm and said U shaped aligning means extends substantially along the entire length of said at least one of said blades.

8. The apparatus of claim 6 wherein said U shape aligning means has an upper leg and a lower leg, the lower leg of said U shaped aligning means being longer than the upper leg, said legs of said U shaped aligning means are substantially perpendicular to said planar member.

9. The apparatus of claim 8 in which said blades are maintained on said arms in a perpendicular orientation in relationship to the arms.

10. The apparatus of claim 8 in which the length of the upper leg is less than the depth of the narrowed portion as measured normal to one of said arms.

11. The apparatus of claim 1 in which said arms have a hinged portion.

* * * * *